(12) United States Patent
Dizigan et al.

(10) Patent No.: US 8,236,938 B2
(45) Date of Patent: *Aug. 7, 2012

(54) HIGH LYSINE MAIZE COMPOSITIONS AND METHODS FOR DETECTION THEREOF

(75) Inventors: Mark A. Dizigan, Cranston, RI (US); Rebecca A. Kelly, South Kingstown, RI (US); Dale A. Voyles, Pawcatuck, CT (US); Michael Hans Luethy, Webster Groves, MO (US); Thomas M. Malvar, North Stonington, CT (US); Kathleen P. Malloy, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/590,529

(22) Filed: Nov. 9, 2009

(65) Prior Publication Data
US 2010/0212051 A1 Aug. 19, 2010

Related U.S. Application Data

(62) Division of application No. 11/542,046, filed on Oct. 3, 2006, now Pat. No. 7,615,621, which is a division of application No. 11/004,221, filed on Dec. 2, 2004, now Pat. No. 7,157,281.

(60) Provisional application No. 60/529,182, filed on Dec. 11, 2003.

(51) Int. Cl.
 C07H 21/04 (2006.01)
 C12Q 1/68 (2006.01)
 C12P 19/34 (2006.01)
 C12N 5/04 (2006.01)
 C12N 5/10 (2006.01)
 A01H 5/00 (2006.01)

(52) U.S. Cl. .............. 536/23.1; 536/24.3; 536/24.33; 435/6.1; 435/6.11; 435/6.12; 435/91.2; 435/419; 800/298; 800/320.1

(58) Field of Classification Search .................. None
See application file for complete search history.

(56) References Cited

U.S. PATENT DOCUMENTS

| | | | |
|---|---|---|---|
| 5,258,300 | A | 11/1993 | Glassman et al. |
| 5,286,632 | A | 2/1994 | Jones |
| 5,658,772 | A | 8/1997 | Odell et al. |
| 5,773,691 | A | 6/1998 | Falco et al. |
| 6,329,574 | B1 | 12/2001 | Lundquist et al. |
| 6,444,884 | B1 | 9/2002 | Johnson |
| 6,459,019 | B1 | 10/2002 | Falco et al. |
| 6,825,400 | B2 | 11/2004 | Behr et al. |
| 7,071,383 | B2 | 7/2006 | Falco |
| 7,157,281 | B2 | 1/2007 | Dizigan et al. |
| 2004/0234960 | A1 | 11/2004 | Olek et al. |
| 2005/0005330 | A1 | 1/2005 | Falco et al. |

FOREIGN PATENT DOCUMENTS

| | | |
|---|---|---|
| CA | 2280196 A | 10/1998 |
| WO | WO 98/53083 | 11/1998 |
| WO | WO 00/63401 | 10/2000 |
| WO | WO 02/18632 A2 | 3/2002 |

OTHER PUBLICATIONS

Falco, S. C., et al., Transgenic canola and soybean seeds with increased lysine, *BioTechnology* 13:577-582 (Jun. 1995) [labeled XP-002035500].
Frisch, D. A., et al., Direct genetic selection of a maize cDNA for dihydrodipicolinate synthase in an *Escherichia coli* dapA auxotroph, *Molecular and General Genetics* 228:287-293 (1991).
McElroy, David L., et al., Isolation of an efficient actin promoter for use in rice transformation, *The Plant Cell* 2:163-171 (Feb. 1990) [labeled XP-002118812].
EMBL Online Database Accession No. CC633189, *Zea mays* genomic clone ZMMBMa0318N05 genomic survey sequence, Jun. 2003 [C. A. Whitelaw, et al.], http://www.ebi.ac.uk/embl/ [labeled XP-002345080].
EMBL Online Database Accession No. BZ681205, *Zea mays* genomic clone ZMMBTa041B07, *DNA sequence*, Feb. 2003 [C. A. Whitelaw, et al.], http://www.ebi.ac.uk/embl/ [labeled XP-002345083].
EMBL Online Database Accession No. CG176305, *Zea mays* genomic clone ZMMBTa0745H14, *genomic survey sequence*, Aug. 2003 [C. A. Whitelaw, et al.], http://www.ebi.ac.uk/embl/ [labeled XP-002345082].
EMBL Online Database Accession No. CG054145, *Zea mays* genomic clone ZMMBTa0706P15, *genomic survey sequence*; Aug. 2003 [C. A. Whitelaw, et al.], http://www.ebi.ac.uk/embl/ [labeled XP-002345081].
GenBank accession No. CG440474, *Zea mays* (online Sep. 17, 2003) [C. A. Whitelaw, et al., unpublished].
Ahern, Holly. Biochemical, reagent kits offer scientists good return on investment, *The Scientist* 9(15):20-24 (Jul. 24, 1995) [accessed at http://www.the-scientist.library.upenn.edu/yr1995/july/tools_950724.html] [see also www.the-scientist.com].

*Primary Examiner* — Gary Benzion
*Assistant Examiner* — Angela M Bertagna
(74) *Attorney, Agent, or Firm* — Winston & Strawn LLP

(57) ABSTRACT

Disclosed herein are assays for detecting the presence of a lysine-increasing transgenic event based on the DNA sequence of the exogenous DNA construct inserted into the maize genome and of genomic sequences flanking the insertion site. Also provided are transgenic plants having a novel exogenous DNA construct that expresses a dihydrodipicolinic acid synthase, the activity of which results in increased lysine in a plant or plant product.

11 Claims, 2 Drawing Sheets

AGGATCCGAGCGGAGTTATGGGTCGACGGTATCGATAAG
Portion of maize genomic DNA    Portion of 5' transgene CACTAGTAACGGCCGCCATAATTATTGCCCAGTCTTTC
Portion of 3' transgene    Portion of maize genomic DNA

HIGH LYSINE MAIZE COMPOSITIONS AND METHODS FOR DETECTION THEREOF

CROSS REFERENCES TO RELATED APPLICATIONS

This application is a divisional of application Ser. No. 11/542,046 filed Oct. 3, 2006, now U.S. Pat. No. 7,615,621 which is a divisional of Ser. No. 11/004,221 filed Dec. 2, 2004, issued U.S. Pat. No. 7,157,281, which claims benefit of priority from U.S. Provisional Patent Application No. 60/529,182, all of which are hereby incorporated by reference herein in their entirety.

FIELD OF THE INVENTION

The present invention relates to the field of plant molecular biology. More specifically, the present invention relates to transgenic maize with increased lysine, and to assays and methods for identifying the specific exogenous DNA providing increased lysine.

BACKGROUND OF THE INVENTION

*Zea mays*, commonly known as maize and corn, is a grain widely used in animal feed. The grain, i.e., kernel, is a source of protein, starch, and oil for swine, cattle, and poultry. Of the ten amino acids deemed essential in a mixed grain feed source, corn is particularly limiting in lysine, threonine, and methionine. The lack of these amino acids, especially lysine, requires that feed corn or corn meal be supplemented with these nutrients, often provided by the addition of soybean meal. It would be of benefit to the art to increase the level of lysine in corn kernel as a means of making the seed and meal more nutritious as an animal feed.

In order to increase levels of lysine using a molecular biological approach, a feedback-insensitive version of at least one of the lysine pathway enzymes, namely dihydrodipicolinic acid synthase (referred to herein as DHDPS), has been identified and employed. A bacterial DHDPS gene isolated from *E. coli* has been shown in vitro to be about 200-fold less sensitive to inhibition by increases in lysine levels and, when introduced into transgenic tobacco, over-expression of the *E. coli* DHDPS gene resulted in increased levels of lysine in leaf tissue (Glassman et al., U.S. Pat. No. 5,288,300). Falco et al. disclose transgenic plants with increased levels of lysine in the seed and genes useful for the production of such transgenic plants (U.S. Pat. Nos. 5,773,691 and 6,459,019; U.S. Patent Application Publication 2003/0056242, each of which is incorporated herein by reference in its entirety). In these reports, Falco et al. describe the isolation and use of feedback-insensitive DHDPS from *E. coli* and DHDPS from *Corynebacterium* (also known as cordapA) to generate transgenic rapeseed, tobacco, maize, and soybean plants with increased levels of lysine in the seed. For maize, Falco et al. report an approximately 130% increase in free lysine in kernels transformed with the cordapA gene relative to non-transformed kernels.

It would be advantageous to be able to detect the presence or absence of a particular transgene in a plant or seed, or progeny of such plants or seeds, not only with respect to the transgene itself, but also with respect to its location in the genome of a host plant or seed. Identification with respect to location further provides identification of the transgenic event by which a genetic engineer inserted the transgene into the progenitor plant of the plant or seed.

SUMMARY OF THE INVENTION

The present invention provides constructs useful for generating transgenic events and materials and methods useful for identifying particular transgenic events that resulted in transgenic plants that accumulate higher levels of lysine than do closely related plants that do not include the construct. In particular, this invention comprises a line of marker-free transgenic maize comprising a specific exogenous DNA that was introduced via standard maize transformation, referred to herein as "the LY038 Event" or "Event LY038." The present invention further provides a method for detecting the presence or absence of the LY038 Event in DNA obtained from maize plants, seeds, or tissue samples. The maize plant of the present invention comprising Event LY038 exhibits increased lysine in the kernel relative to a progenitor or other substantially related plant. In addition, the present invention provides an exogenous DNA construct comprising a maize globulin 1 promoter, a rice actin 1 intron, a maize dihydrodipicolinate synthase chloroplast transit peptide-encoding DNA molecule, a *Corynebacterium* dihydrodipicolinate synthase-encoding DNA molecule, and a maize globulin 1 3' untranslated region that, when operably linked and expressed in transgenic plant cells and plants, results in increased lysine content in the kernel or parts thereof or a processed product derived from the kernel or plant. In another embodiment, the construct further comprises a lox site, present as a component of a mechanism for removing the marker gene used to identify successful transformants.

With respect to identifying a plant or seed derived from a particular transgenic event, compositions and methods are provided for detecting the presence of the genomic insertion region from a novel maize plant comprising Event LY038, i.e., the site in the genome where the construct resides. DNA molecules are provided that comprise at least a portion of the exogenous DNA inserted into the genome and a portion of the DNA from the maize genome flanking the insertion site (referred to herein as a "junction sequence").

In yet another embodiment of the present invention, novel DNA molecules are provided that comprise at least about 20 base pairs of SEQ ID NO: 1 or 2, where base pairs 1781-1782 or 200-201, respectively, are included. Further provided by the present invention are DNA molecules comprising the sequence of an amplicon having the sequence of SEQ ID NO: 6 obtained by a DNA amplification method using primers of SEQ ID NOs: 3 and 4; and a hybridization probe complementary to said amplicon, having the sequence of SEQ ID NO: 5 and complements thereof. DNA molecules having the sequence of SEQ ID NO: 5 or 6 span the junction between the exogenous DNA and flanking maize genomic DNA and are diagnostic for Event LY038 DNA when used in suitable analytical tests. Other preferred DNA molecules of the present invention that span the junction of the exogenous DNA/genomic insertion region of Event LY038 are molecules having the sequence of SEQ ID NOs: 1, 2, and 11, and complements thereof. A stably transformed maize plant or seed comprising these molecules is another aspect of this invention.

Primers are said to be of "sufficient length" when they are of a length that allows the primer to function in a PCR reaction and specifically amplify a target sequence; a length of about 11 nucleotides or more is sufficient, more preferably about 18 nucleotides or more, yet more preferably about 24 nucleotides or more, even more preferably about 30 nucleotides is sufficient to perform and specifically amplify a target sequence. One skilled in the art would know that a primer of even greater length than about 30 nucleotides can be usefully employed in a PCR reaction and, accordingly, is of a sufficient length.

PCR primers useful for identifying Event LY038 comprise a sufficient length of a transgene portion of the DNA sequence of SEQ ID NO: 1 and a sufficient length of a 5' flanking maize DNA sequence of SEQ ID NO: 1, or a sufficient length of a transgene portion of the DNA sequence of SEQ ID NO: 2 and a sufficient length of a 3' flanking maize DNA sequence of SEQ ID NO: 2. These primers are useful in PCR methods to provide a DNA amplicon product that is diagnostic for Event LY038 and its progeny. PCR primers homologous or complementary to any suitable length of SEQ ID NOs: 1 and 2 that can produce an amplicon or probe that is diagnostic for Event LY038 are another aspect of the present invention. For example, without limitation, preferred primers that are diagnostic for Event LY038 include those having at least about 18 contiguous nucleotides of either of the sequences of SEQ ID NO: 3 or 4. The amplicons produced using DNA primers that are diagnostic for Event LY038 and its progeny are an aspect of this invention. A preferred amplicon diagnostic for Event LY038 has the sequence of SEQ ID NO: 6.

Another aspect of the present invention provides methods of detecting the presence or absence of DNA corresponding to Event LY038 in a sample. Such methods comprise obtaining DNA from a maize plant, seed, or tissue, contacting the sample DNA with a PCR primer set, performing PCR and detecting the presence or absence of an amplicon. Preferred PCR primers diagnostic for Event LY038 include oligonucleotide primers having the sequence of SEQ ID NOs: 3 and 4, which produce an LY038 event-specific amplicon having the sequence of, for example, SEQ ID NO: 6, which is detectable by an LY038 event-specific probe having the sequence of, for example, SEQ ID NO: 5.

Hybridization of a probe indicating the presence of Event LY038 to an amplicon comprising DNA specific to Event LY038 may be detected by any suitable means available to nucleic acid manipulation arts, including TaqMan® assays, Southern blot methods among other methods known to those of ordinary skill in the art of molecular biology. One skilled in the art would know that the detecting of the amplicon may be carried out by means of detection that do not involve hybridization of a probe to an amplicon, such as acrylamide gel or agarose gel analyses. One skilled in the art would also know that both the length and sequence of both the primer and probe may be varied from the exemplified sequences presented in SEQ ID NOs: 3, 4, and 5, and still produce a PCR amplicon, or amplicon and probe set, that is diagnostic for Event LY038.

In another aspect, the present invention provides a method for producing progeny plants comprising Event LY038 DNA. The progeny plants may be inbred or hybrid plants. In a further application, the present invention provides a method for performing marker-assisted breeding for Event LY038 DNA. According to another aspect of the present invention, a stably transformed maize plant comprising Event LY038 DNA and further comprising increased lysine in the kernel or parts thereof is provided.

The present invention further relates to a DNA detection kit comprising at least one DNA molecule of sufficient length of contiguous nucleotides homologous or complementary to SEQ ID NO: 1 or 2, that functions as a DNA primer or probe specific for Event LY038 or its progeny.

This present invention further relates to the plants and seeds and processed products thereof of high lysine maize (*Zea mays*) comprising Event LY038 and the progeny derived thereof having representative seed deposited as ATCC Accession No. PTA-5623. Additionally provided by the present invention is a maize plant or a part thereof, including, for example, pollen or seed, produced by growing a plant that comprises Event LY038 DNA. The maize plant and seed comprising Event LY038 DNA for which the DNA primer molecules of the present invention are usefully employed for detection of the event-specific sequences are further aspects of the invention.

A processed product of LY038 Event comprises a part of a maize kernel, for example, the endosperm. A maize meal of the present invention can be made from the kernel comprising the transgenic DNA molecule of LY038, wherein the meal is high in lysine relative to other maize meals not containing the DNA molecule.

The foregoing and other aspects of the present invention will become more apparent from the following detailed description, examples, and accompanying figures. The following examples are included to demonstrate examples of certain preferred embodiments of the present invention. It should be appreciated by those of skill in the art that the techniques disclosed in the examples that follow represent approaches the inventors have found function well in the practice of the present invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

BRIEF DESCRIPTION OF SEQUENCES

Molecules having defined sequences used in the context of the present invention are set forth in the Sequence Listing filed concomitantly with this application. A summary of the Sequence Listing follows:

SEQ ID NO: 1 is a 1961 base pair (bp) polynucleotide sequence of the 5' DNA comprising the maize genomic portion (bp 1-1781) flanking the 5' side of the insertion site and transgene insert portion (bp 1782-1961) of the LY038 event DNA.

SEQ ID NO: 2 is an 867 bp polynucleotide sequence of the 3' DNA comprising the 3' maize genomic portion (bp 201-867) flanking the 3' side of the insertion site and transgene insert sequence (bp 1-200) of the LY038 Event DNA.

SEQ ID NOs: 3 and 4 are polynucleotide sequences of PCR primers useful for producing an amplicon diagnostic for Event LY038 DNA.

SEQ ID NO: 5 is a polynucleotide sequence of an oligonucleotide probe useful for hybridizing to an amplicon for detecting Event LY038 DNA.

SEQ ID NO: 6 is a polynucleotide sequence of an amplicon diagnostic for Event LY038 DNA.

SEQ ID NO: 7 is a polynucleotide sequence of a maize globulin 1 promoter (bp 48 to 1440; Kriz, *Biochem. Genet.*, 27:239-251, 1989; Belanger and Kriz, *Genetics*, 129:863-

872, 1991; U.S. Pat. No. 6,329,574, incorporated herein by reference in its entirety), a rice actin 1 intron (bp 1448 to 1928; McElroy et al., *Plant Cell*, 2:163-171, 1990), a maize DHDPS chloroplast transit peptide (bp 1930 to 2100; Frisch et al., *Mol. Gen. Genet.*, 228:287-293, 1991), a *Corynebacterium* DHDPS gene (bp 2101 to 3003; Bonnassie et al., *Nucleic Acids Research*, 18:6421, 1990); Richaud et al., *J. Bacteriol.*, 166:297-300, 1986), a maize globulin 1 3' untranslated region (bp 3080 to 4079; Belanger and Kriz, supra), and a lox P site (bp 4091 to 4124; Russell et al., *Mol. Gen. Genet.*, 234:45-59, 1992).

SEQ ID NO: 8 is a polynucleotide sequence of a *Corynebacterium* DHDPS gene (Bonnassie et al., *Nucleic Acids Research*, 18:6421, 1990; Richaud et al., *J. Bacteriol.*, 166: 297-300, 1986).

Figures 2A, 2B, 2C:
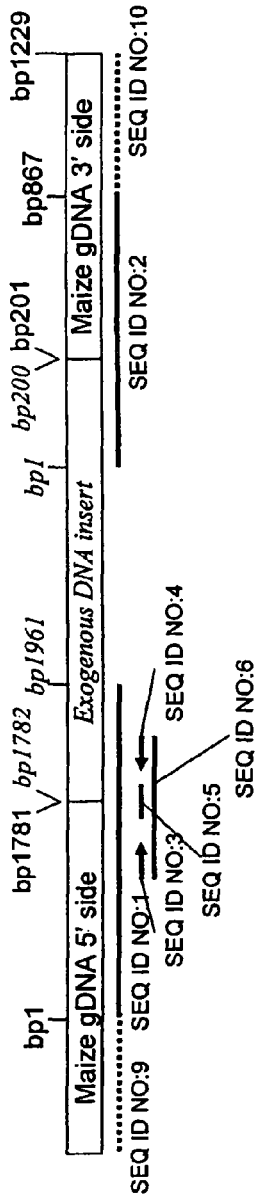
FIG. 2A is a schematic of exogenous DNA insertion Event LY038. Exogenous DNA and pertinent base pairs are indicated by italic font, maize genomic DNA and pertinent base pairs are indicated by regular font.
FIG. 2B is the sequence at the 5' junction. It depicts nucleotides 1761 to 1800 of SEQ ID NO:1 for Event LY038.
FIG. 2C is the sequence at the 3' junction. It depicts nucleotides 184 to 221 of SEQ ID NO:2 for Event LY038.

SEQ ID NO: 9 is a 1736 base pair polynucleotide sequence of additional maize genomic DNA flanking the 5' side of the insertion site of the LY038 event (see FIG. 2A).

SEQ ID NO: 10 is a 359 base pair polynucleotide sequence of additional maize genomic DNA flanking the 3' side of the insertion site of the LY038 event (see FIG. 2A).

SEQ ID NO: 11 is a 20 base pair polynucleotide sequence consisting of 10 contiguous nucleotide of transgene insert DNA and 10 contiguous nucleotides of maize genomic DNA of the junction sequence illustrated in FIG. 2C.

DETAILED DESCRIPTION OF THE INVENTION

As used herein, "exogenous DNA" refers to DNA that does not naturally originate from the particular construct, cell, or organism in which that DNA is found. Exogenous DNA may include a DNA or RNA sequence native to a genome but in a new location in the genome or linked to other sequence elements not naturally associated with the exogenous DNA in its native state. Recombinant DNA constructs used for transforming plant cells comprise exogenous DNA and usually other elements as discussed below. As used herein "transgene" means an exogenous DNA that has been incorporated into a host genome or is capable of autonomous replication in a host cell and is capable of causing the expression of one or more cellular products. Exemplary transgenes provide the host cell or plants regenerated therefrom, with a novel phenotype relative to the corresponding non-transformed progenitor cell or plant, or a corresponding transformed progenitor cell or plant comprising other transgenes but not the particular transgene in question. Transgenes may be directly introduced into a plant by genetic transformation, or may be inherited from a plant of any previous generation that was transformed with the exogenous DNA.

As used herein, "gene" or "coding sequence" means a DNA sequence from which an RNA molecule is transcribed. The RNA may be an mRNA that encodes a protein product, an RNA that functions as an anti-sense molecule, or a structural RNA molecule such as a tRNA, rRNA, snRNA, or other RNA. As used herein "expression" refers to the combination of intracellular processes, including transcription and translation, by which a DNA molecule, such as a gene, is employed to produce a polypeptide or an RNA molecule. An exemplary coding sequence is a *Corynebacterium* dihydrodipicolinate synthase gene (DHDPS; Bonnassie et al., *Nucleic Acids Research*, 18:6421, 1990; Richaud et al., *J. Bacteriol.*, 166: 297-300, 1986; by 2101 to 3003 of SEQ ID NOs: 7 and 8), useful for the production of maize kernels with increased lysine. A maize plant, transformed to contain and express a *Corynebacterium* DHDPS gene resulting in increased lysine in kernel tissue, is also referred to as a high lysine maize plant.

As used herein, "promoter" means a region of DNA sequence that is essential for the initiation of transcription of DNA, resulting in generation of an RNA that is complementary to the transcribed DNA; this region may also be referred to as a "5' regulatory region." Promoters are located upstream of the coding sequence to be transcribed and have regions that act as binding sites for RNA polymerase and have regions that work with other factors to promote RNA transcription. Useful plant promoters include those that are constitutive, inducible, tissue-specific, temporally regulated, circadian in regulation, drought inducible, stress inducible, developmentally regulated, cold inducible, light inducible, and the like. Of particular importance to the present invention is an embryo-specific promoter, such as, without limitation, the maize globulin 1 promoter (Kriz, *Biochem. Genet.*, 27:239-251, 1989; Belanger and Kriz, *Genetics*, 129:863-872, 1991; by 48 to 1440 of SEQ ID NO: 7).

As is well known in the art, recombinant DNA constructs typically also comprise other regulatory elements in addition to a promoter, such as but not limited to 3' untranslated regions (such as polyadenylation sites or transcriptional termination signals), transit or signal peptides, introns, and marker genes elements. A 3' untranslated region (3' UTR) useful in the practice of the present invention is the globulin 1 3' UTR (Kriz, *Biochem. Genet.*, 27:239-251, 1989; Belanger and Kriz, *Genetics*, 129:863-872, 1991; by 3080 to 4079 of SEQ ID NO: 7). A particularly useful transit peptide is the maize DHDPS transit peptide (Frisch et al., *Mol. Gen. Genet.*, 228:287-293, 1991; by 1930 to 2100 of SEQ ID NO: 7). An intron useful in the context of the present invention is the rice actin 1 intron 1 (McElroy et al., *Plant Cell*, 2:163-171, 1990; by 1448 to 1928 of SEQ ID NO: 7).

As used herein, the term "maize" means *Zea mays*, also known as corn, and includes all plant varieties that can be bred with maize, including wild maize species. Methods and compositions for transforming plants by introducing an exogenous DNA into a plant genome in the practice of this invention can include any of the well-known and demonstrated methods. To date, microparticle- and *Agrobacterium*-mediated gene delivery are the two most commonly used plant transformation methods. Microparticle-mediated transformation refers to the delivery of DNA coated onto microparticles that are propelled into target tissues by several methods. *Agrobacterium*-mediated transformation is achieved through the use of a genetically engineered soil bacterium belonging to the genus *Agrobacterium*. Several *Agrobacterium* species mediate the transfer of a specific DNA known as "T-DNA," which can be genetically engineered to carry any desired piece of DNA into many plant species. Preferred methods of plant transformation are microprojectile bombardment as illustrated in U.S. Pat. Nos. 5,015,580; 5,550,318; 5,538,880; 6,160,208; 6,399,861; and 6,403,865; and *Agrobacterium*-mediated transformation as illustrated in U.S. Pat. Nos. 5,635,055; 5,824,877; 5,591,616; 5,981,840; and 6,384,301, all of which are incorporated herein by reference.

As used herein a "transgenic" organism is one whose genome has been altered by the incorporation of foreign genetic material or additional copies of native genetic material, e.g. by transformation or recombination. The transgenic organism may be a plant, mammal, fungus, bacterium, or virus. As used herein "transgenic plant" means a stably transformed plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences that are native to the plant being transformed, but wherein the exogenous DNA has been altered in order to alter the level or pattern of expression of the gene.

As used herein, a "stably" transformed plant is a plant in which the exogenous DNA is heritable. The exogenous DNA may be heritable as a fragment of DNA maintained in the plant cell and not inserted into the host genome. Preferably, the stably transformed plant comprises the exogenous DNA inserted into the chromosomal DNA in the nucleus, mitochondria, or chloroplast, most preferably in the nuclear chromosomal DNA.

As used herein a "$R_o$ transgenic plant" is a plant that has been directly transformed with an exogenous DNA or has been regenerated from a cell or cell cluster that has been transformed with an exogenous DNA. As used herein "progeny" means any subsequent generation, including the seeds and plants therefrom, which is derived from a particular parental plant or set of parental plants; the resultant progeny line may be inbred or hybrid. Progeny of a transgenic plant of this present invention can be, for example, self-crossed, crossed to a transgenic plant, crossed to a non-transgenic plant, and/or back crossed.

The seeds of the plants of this present invention can be harvested from fertile transgenic plants and be used to grow progeny generations of plants of this present invention, including a hybrid plant line comprising the exogenous DNA of Event LY038, which provides the benefit of increased lysine in the maize kernel. The maize kernel may be processed into meal and oil products or the kernel can fed to animals without processing. The meal product in particular contains an enhanced agronomic trait, increased lysine. The present invention contemplates a maize meal with increased lysine relative to other maize meals, wherein the maize meal comprises the exogenous DNA of Event LY038.

The term "Event LY038 DNA" refers to a DNA segment comprising an exogenous DNA inserted into a particular location in a genome and adjacent flanking genomic DNA that would be expected to be transferred to a progeny plant from a parent plant containing the exogenous DNA. More specifically, Event LY038 DNA also refers to each of the DNA regions that include an interface of the genomic DNA and the inserted exogenous DNA in the genome of the $R_o$ transformant, e.g., a region around one interface where the 5' end is in genomic DNA and the 3' end is in exogenous DNA. In addition, the sequence of the exogenous DNA comprising an event DNA may be altered while resident in its particular location in a host genome, e.g., a portion of the sequence may be changed, deleted, or amplified, and still constitute said event DNA providing said exogenous DNA continues to reside in the same location in the genome.

A transgenic "event" is produced by transformation of a plant cell with an exogenous DNA construct, the regeneration of a plant resulting from the insertion of the exogenous DNA into the genome of the plant, and selection of a particular plant characterized by event DNA. Typically, a number of plant cells are transformed, producing a population of plants from which a particular plant is selected. The term "event" refers to the original $R_o$ transformant and progeny of the transformant that include the exogenous DNA inserted into a particular and unique location in the genome, i.e., event DNA. The term "event" also refers to progeny produced by a sexual outcross, a self-cross, or repeated backcrossing, wherein at least one of the plants used in the breeding are of any generation of the original $R_o$ transformant containing event DNA.

Thus, a transgenic "event" is a plant comprising and defined by an "event DNA." In this way, "Event LY038" comprises "LY038 Event DNA." A plant may comprise two or more different event DNAs and thus comprise two or more different events. In addition, a plant lacking a given transgene event X does not comprise that event DNA X in question. Event DNA may be transferred from plant to plant, generation to generation, by any breeding scheme, method, or tool known to those of skill in the art of maize breeding.

Transformation of plants typically utilizes a selectable marker and selection method to distinguish the transformed cells of the culture from the non-transformed cells. In some instances the selectable marker gene remains in the transgenic plant; in other instances it is desirable to remove the selectable marker gene or other sequences introduced in the exogenous DNA. Homologous recombination is one method useful for the deletion of marker genes residing within a transgenic plant (U.S. Pat. No. 6,580,019, incorporated herein by reference in its entirety). Another useful tool for removing sequences from a plant involves the use of site-specific recombinase enzymes and their respective site-specific target sites.

A number of different site-specific recombinase systems could be employed in accordance with the instant invention, including, but not limited to, the Cre/lox system of bacteriophage P1, and the FLP/FRT system of yeast. The bacteriophage P1 Cre/lox and the yeast FLP/FRT systems constitute two particularly useful systems for site-specific integration or excision of transgenes. In these systems, a recombinase (Cre or FLP) will interact specifically with its respective site-specific recombination sequence (lox or FRT, respectively) to invert or excise the intervening sequences. The sequence for each of these two systems is relatively short (34 bp for lox and 47 bp for FRT) and therefore, convenient for use with transformation vectors. The FLP/FRT and Cre/lox recombinase systems have been demonstrated to function efficiently in plant cells. In a preferred embodiment, a Cre/lox recombinase system is employed to removed selectable marker sequences, particularly an NPT II marker gene (see FIG. 1) flanked by lox P recombination sites (bp 4091 to 4124 SEQ ID NO: 7; Russell et al., *Mol. Gen. Genet.*, 234:45-59, 1992).

A transgenic plant, seed or parts thereof, that shows an enhanced desired trait, e.g., "increased lysine," is a plant comprising an exogenous DNA that imparts a desired, measurable change in a trait in comparison to a plant of substantially the same genotype that lacks the desired exogenous DNA. Preferably, the enhanced desired trait is measured by comparing the trait in a transgenic plant with the exogenous DNA associated with the enhanced desired trait to the trait in a plant of substantially the same genotype but lacking that exogenous DNA. Such a plant that lacks that exogenous DNA can be a natural wild-type plant or a transgenic plant, preferably of the same species as the transgenic plant. Preferably, the plant lacking the exogenous DNA is a sibling lacking the desired exogenous DNA of the plant comprising the desired exogenous DNA. Such a sibling plant may comprise other exogenous DNAs. Increased lysine may be exhibited by the plant by accumulation of increased amounts of the amino acid in the kernel and may be measured by any suitable method, such as that of mass spectrophotometry or high performance liquid chromatography of appropriately extracted tissue.

As used herein, a "probe" is an isolated oligonucleotide to which may be attached a detectable label or reporter molecule, e.g., a radioactive isotope, ligand, chemiluminescent agent, dye, or enzyme. Such a probe is complementary to a strand of a target nucleic acid. In the case of the present invention, such a probe is complementary to a strand of genomic DNA from Event LY038, e.g., genomic DNA from a maize plant or seed or other plant part of Event LY038. Probes according to the present invention are materials, including DNA, RNA, and polyamides, that bind specifically to a target DNA sequence and can be used to detect the presence of that target DNA sequence.

"Primers" are isolated oligonucleotides that can anneal to a complementary target DNA strand by nucleic acid hybridization and then be extended along the target DNA strand by a polymerase, e.g., a DNA polymerase. As used herein, primers of the present invention are used for DNA amplification of a target nucleic acid sequence, for example, by the polymerase chain reaction (PCR) and may also be referred to as "PCR primers."

Probes and primers are of sufficient nucleotide length to bind to the target DNA sequence specifically under the hybridization conditions or reaction conditions determined by a skilled artisan. This length may be any length that is of sufficient length to be useful in the detection method of choice. Generally, about 11 nucleotides or more in length, preferably about 18 nucleotides or more, more preferably about 24 nucleotides or more, and, most preferably, about 30 nucleotides or more are used. Such probes and primers hybridize specifically to a target. Preferably, probes and primers according to the present invention have complete DNA sequence similarity of contiguous nucleotides with the target sequence, although probes differing from the target DNA sequence and that retains the ability to hybridize to target DNA sequences may be designed by conventional methods. Methods for preparing and using probes and primers are known to those of skill in the art, using protocols published in, for example, Sambrook et al., *Molecular Cloning: A Laboratory Manual, Second Edition*, Cold Spring Harbor Laboratory Press, 1989, and the like.

Identification of the flanking genomic DNA sequences surrounding the insertion site of transgenic events allow for the design of detection methods that are specific for a given transgenic event inserted into a particular location in a genome. Such a detection method, which can differentiate between the same or similar transgenes located in different insertion sites in a genome, is termed an event-specific DNA detection method, e.g., an event-specific assay. Event-specific assays, for example, for glyphosate tolerant maize event nk603 have been described (U.S. Patent Application Publication 2002/0013960, incorporated herein by reference in its entirety).

In a preferred embodiment, a nucleic acid probe of the present invention specifically hybridizes to the LY038 Event-specific amplicon having the nucleic acid sequence of SEQ ID NOs: 3-6, or complements thereof, most preferably SEQ ID NO: 5 or complements thereof. In another aspect of the present invention, a preferred nucleic acid probe molecule of the present invention shares between about 80%, preferably about 90%, more preferably about 95%, even more preferably about 98%, and most preferably about 99% sequence identity with the nucleic acid sequence set forth in one or more of SEQ ID NOs: 3-6, or complements or fragments thereof. Exemplary probes diagnostic for Event LY038 have the sequence of SEQ ID NO: 6. Such probe molecules may be used by those of skill in the art as markers in plant breeding methods to identify the progeny of genetic crosses. The hybridization of the probe to the target DNA molecule can be detected by any number of methods known to those skilled in the art. These detection methods can include, but are not limited to, fluorescent tags, radioactive tags, antibody based tags, and chemiluminescent tags.

As used herein, "homologous" refers to a nucleic acid sequence that will specifically hybridize to the complement of the nucleic acid sequence to which it is being compared under high stringency conditions. Appropriate stringency conditions, including those conditions of time, temperature, and salt condition, that promote DNA hybridization are known to those skilled in the art. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NO: 1 or 2, or complements thereof or fragments of either under strong to moderately stringent conditions. In a particularly preferred embodiment, a nucleic acid of the present invention will specifically hybridize to one or more of the nucleic acid molecules set forth in SEQ ID NO: 1 or 2 or complements or fragments of either under high stringency conditions. The hybridization of the probe to the target DNA molecule can be detected by any number of methods known to those skilled in the art, these can include, but are not limited to, fluorescent tags, radioactive tags, antibody based tags, and chemiluminescent tags.

As used herein, "amplicon" refers to the product of nucleic-acid amplification of a target nucleic acid sequence that is part of a nucleic acid template. For example, to determine whether the maize plant resulting from a sexual cross contains transgenic event genomic DNA from the maize plant comprising exogenous LY038 DNA, DNA extracted from a maize plant tissue sample may be subjected to a nucleic acid amplification method using a DNA primer pair that includes a first primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about 20 nucleotide base pairs, more preferably plus about 50 nucleotide base pairs, and even more preferably plus about 150 nucleotide base pairs and more depending on the method used to detect the amplicon. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to the limits of the amplification reaction, or about 20,000 nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). The sequence of the heterologous DNA insert or flanking DNA sequence from Event LY038 can be verified (and corrected if necessary) by amplifying such sequences from DNA extracted from the ATCC deposit Accession No. PTA-5623 seed or plants using DNA primers derived from the sequences provided herein followed by standard DNA sequencing of the PCR amplicon or of the cloned DNA.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

Amplicons produced by amplification methods may be detected by a plurality of techniques, including but not limited to gel based analyses, genetic bit analysis (Nikiforov et al., *Nucleic Acid Res.*, 22:4167-4175, 1994), pyrosequencing (Winge, M., Pyrosequencing—a new approach to DNA analysis, (2000), Innovations in Pharmaceutical Technology, vol 00, 4, p 18-24), fluorescence polarization (Chen et al., *Genome Res.*, 9:492-498; 1999), and molecular beacons (Tyangi et al., *Nature Biotech.*, 14:303-308, 1996).

Of particular interest to the present invention is detection by Taqman® assay (available from Applied Biosystems, Foster City, Calif.). Taqman® assay is a method of detecting and quantifying the presence of a DNA sequence that is well known in the art, and is fully described in the instructions provided by the manufacturer. This method involves the use of PCR amplification and detection of the amplification product by hybridization using a special FRET oligonucleotide probe. The FRET oligonucleotide probe is designed to have a 5' fluorescent reporter dye and a 3' quencher dye covalently linked to the 5' and 3' ends of the probe. The probe is designed to overlap the junction of the genomic DNA and inserted DNA. The FRET probe and PCR primers (one primer in the exogenous transgene DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

PCR primers preferable for use with Taqman® assay are designed (a) to have a length in the size range of 18 to 25 bases and matching sequences in the flanking genomic DNA and the transgene insertion, (b) to have a calculated melting temperature in the range of about 57 to about 60° C., e.g., corresponding to an optimal PCR annealing temperature of about 52 to about 55° C., and (c) to produce a product that includes the junction between the flanking genomic DNA and the transgene insertion and has a length in the size range of about 75 to about 250 base pairs. The PCR primers are preferably located on the locus so that the junction sequence is at least one base away from the 3' end of each PCR primer. The PCR primers must not contain regions that are extensively self- or inter-complementary.

FRET probes are designed to span the sequence of the junction sequence. In a preferred embodiment, the FRET probes will have incorporated at their 3' end a chemical moiety that, when the probe is annealed to the template DNA, binds to the minor groove of the DNA, thus enhancing the stability of the probe-template complex. The probes preferably have a length in the range of about 12 to about 17 bases, and with the 3' minor groove binding moiety, have a calculated melting temperature of about 5 to about 7° C. above that of the PCR primers. Probe design is disclosed in U.S. Pat. Nos. 5,538,848; 6,084,102; and 6,127,121.

Another assay that employs the sequences of the present invention is that of a zygosity assay. A zygosity assay is useful for determining if a plant comprising an event is homozygous for the event DNA, that is comprising the exogenous DNA in the same location on each chromosome of a chromosomal pair, or heterozygous for an event DNA, that is comprising the exogenous DNA on only one chromosome of a chromosomal pair. In one embodiment, a three primer assay is employed wherein primer 1 hybridizes and extends specifically from the inserted exogenous DNA, primer 2 hybridizes and extends specifically from the DNA flanking the 5' side of the inserted exogenous DNA, and primer 3 hybridizes and extends specifically from the DNA flanking the 3' side of the inserted exogenous DNA. The three primers are diagnostic for the event. Typically, the exogenous DNA is of such a size, e.g., about 3 to about 7 kilobases or more, such that primer 1 and primer 3 no longer produce an amplicon in the PCR reaction. When the three primers are mixed together in a PCR reaction with DNA extracted from a plant homozygous for a given event, a single amplicon is produced by primer 1 and primer 2, the size and sequence of which will be indicative of and diagnostic for the event DNA. When the three primers are mixed together in a PCR reaction with DNA extracted from a plant that does not comprise the given event, a single amplicon is produced by primer 1 and primer 3, the size and sequence of which will be indicative of and diagnostic for maize genomic DNA lacking an exogenous DNA. When the three primers are mixed together in a PCR reaction with DNA extracted from a plant that is heterozygous for a given event, 2 amplicons are produced: 1) an amplicon is produced by primer 1 and primer 3, the size and sequence of which will be indicative of and diagnostic for maize genomic DNA lacking an exogenous DNA, and 2) an amplicon is produced by primer 1 and primer 2, the size and sequence of which will be indicative of and diagnostic for the event DNA. Methods of detecting the various amplicons produced by the zygosity assay are known to those of skill in the art and include, but are not limited to, gel electrophoresis, TaqMan® assays, Southern blot, Invader Technology, sequencing, molecular beacons, pyrosequencing, and the like.

DNA detection kits can be developed using the compositions disclosed herein and the methods well known in the art of DNA detection. The kits are useful for identification of maize Event LY038 DNA in a sample and can be applied to methods for breeding maize plants containing Event LY038 DNA. The kits contain DNA sequences that are useful as primers or probes and that are homologous or complementary to any portion of SEQ ID NO: 1 or 2, or to DNA sequences homologous or complementary to DNA contained in any of the transgene genetic elements of pMON55221 (FIG. 1) that have been inserted into a maize plant genome to form Event LY038 (FIG. 2). These DNA sequences can be used in DNA amplification methods (PCR) or as probes in polynucleic acid hybridization methods, i.e., Southern analysis, or Northern analysis. The DNA molecule (SEQ ID NO:7) contained in the LY038 Event genome comprises the heterologous transgene genetic elements that includes a maize globulin 1 promoter (P-ZM glob1), a rice actin 1 intron (I-Os actin), a maize dihydrodipicolinate synthase chloroplast transit peptide encoding-DNA molecule (Zm DHDPS CTP), a *Corynebacterium* dihydrodipicolinate synthase-encoding DNA molecule (DHDPS), a maize globulin 1 3' untranslated region (T-Zm glob1), and a lox P site and can be used as a template for DNA amplification, or to select homologous or complementary DNA molecules that can be used as a DNA primer or probe in a DNA detection method. The present invention contemplates that one skilled in the art of DNA detection can select one or more DNA molecules homologous or complementary to the transgenic DNA of SEQ ID NO: 7 that is useful in a method to detect the transgenic DNA in the genome of LY038 and progeny thereof.

The following examples are included to demonstrate examples of certain preferred embodiments of the present invention. It should be appreciated by those of skill in the art that the techniques disclosed in the examples that follow represent approaches the inventors have found function well in the practice of the present invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Preparation of Transgenic Plants

Immature embryos of maize line H99 were isolated for transformation. Cassette DNA isolated from vector pMON55221 (see FIG. 1) comprising a maize globulin 1 promoter (Kriz (1989), supra; Belanger and Kriz (1991), supra; U.S. Pat. No. 6,329,574, incorporated herein by reference in its entirety; by 48 to 1440 of SEQ ID NO: 7), a rice actin 1 intron (McElroy et al., (1990), supra; by 1448 to 1928 of SEQ ID NO: 7), a maize DHDPS chloroplast transit peptide encoding DNA molecule (Frisch et al. (1991), supra; by 1930 to 2100 of SEQ ID NO: 7), a *Corynebacterium* dihydrodipicolinate synthase encoding DNA molecule (Bonnassie et al. (1990), supra; Richaud et al. (1986), supra; by 2101 to 3003 of SEQ ID NO: 7), a maize globulin 1 3' untranslated region (Belanger and Kriz (1991), supra; by 3080 to 4079 of SEQ ID NO: 7), a lox P site (U.S. Pat. No. 5,658,772, specifically incorporated herein by reference in its entirety; by 4091 to 4124 of SEQ ID NO: 7), as well as a 35S promoter (Kay et al., *Science*, 236:1299-1302, 1987; U.S. Pat. No. 5,164,316), an NPTII selectable marker encoding DNA molecule (Potrykus et al. (1985), supra), a nos 3' UTR (Fraley et al., *Proc. Natl. Acad. Sci. (U.S.A.)*, 80:4803-4807 (1983), supra), and a lox P site (U.S. Pat. No. 5,658,772, specifically incorporated herein by reference in its entirety) was adhered to gold particles. Microprojectile bombardment was used to introduce the exogenous DNA to the immature maize embryos using methods known to those of skill in the art. Transformed cells were selected using a kanamycin selection scheme. Kanamycin resistant calli were obtained and regenerated into several fertile, $R_o$ transgenic plants using standard methods.

Example 2

Breeding Scheme and Lysine Analysis

Table 1 summarizes the breeding scheme and free lysine data used for the development of maize Event LY038, which exhibits high lysine in maize kernel tissue. Plants produced by the transformation method described in Example 1 were initially screened for the presence or absence of the *Corynebacterium* DHDPS sequence using PCR. Taqman® assay technology was used to determine the number of copies of transgenic insertions. Plants that comprised a DNA molecule having the *Corynebacterium* DHDPS sequence, operably linked as described in Example 1 and FIG. 1, were allowed to reach maturity and to produce $F_{1A}$ seed. For $F_{1A}$ seed production, the primary transgenic $R_o$ plants were crossed with a non-transgenic elite maize inbred line.

Figure 1:
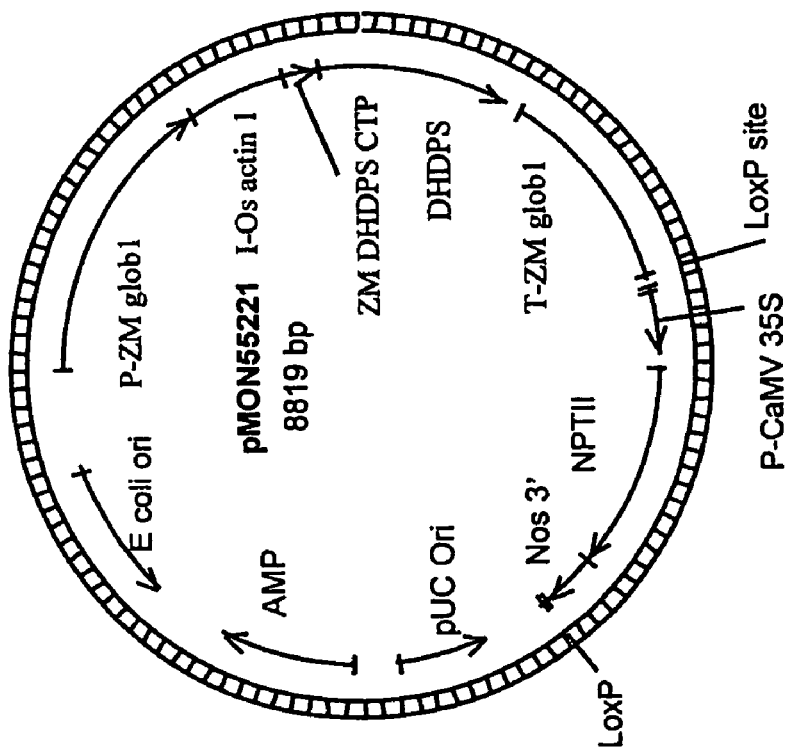
FIG. 1 is a plasmid map of pMON55221.

The $F_{1A}$ plants were screened for the presence or absence of the NPTII sequence as evidenced by using a field scorable kanamycin resistance test. Insensitivity to kanamycin indicated that a plant comprised and was expressing the NPTII marker gene as shown in FIG. 1 and described in Example 1; these plants are referred to hereafter as NPTII+.

NPTII+ plants were crossed with a transgenic maize line expressing a bacterial Cre recombinase to produce $F_{1B}$ seed. The levels of free lysine in a sample of the resulting $F_{1B}$ seed collected from each ear was determined. Sibling $F_{1B}$ kernels exhibiting greater than about 1000 ppm free lysine were advanced to a field nursery. $F_{1B}$ progeny plants were assayed by PCR and/or Southern blot to determine the presence or absence of the DHDPS gene sequence, the Cre recombinase coding sequence and the NPTII selectable marker gene sequence. The NPTII selectable marker gene was flanked by lox P sites (recombination sites) and as such, the activity of the Cre recombinase resulted in the excision of the NPTII coding sequence. Plants comprising the DHDPS and Cre recombinase sequences and lacking the NPTII sequences, referred to hereafter as marker-excised plants, were allowed to self-pollinate to produce $F_{2A}$ seed. Free lysine in the positive and negative $F_{2A}$ seed was determined.

Having obtained $F_{2A}$ seed comprising the exogenous DHDPS gene of interest and lacking the NPTII selectable marker gene, it was now necessary to breed away the Cre recombinase sequences. $F_{2A}$ seed from marker-excised plants were planted in the field and once again assayed by PCR and/or Southern blot to determine the presence or absence of the DHDPS gene sequence, the Cre recombinase coding sequence and the NPTII selectable marker gene sequence. Plants comprising the DHDPS sequence and lacking sequences for both Cre recombinase and NPTII were selected as "positive" plants. Sibling plants lacking the DHDPS, Cre recombinase, and NPTII sequences were selected as "negative" plants to serve as negative controls. Plants comprising the DHDPS sequence were self-pollinated to create $F_3$ seed and advanced to the next generation in the field. Likewise, negative plants lacking the DHDPS, Cre recombinase, and NPTII sequences were self-pollinated to create $F_3$ seed. Free lysine in the positive and negative $F_3$ seed was determined.

Positive plants were grown in the field from $F_3$ seed. A single plant, determined by Taqman® assay to be homozygous, was selected and designated as LY038. $F_3$ plants were either A) self-pollinated to produce $F_{4-38}$ ears, or were B) crossed with an inbred line to produce $F_{1-38A}$ ears of both positive and negative selections. Free lysine in the positive and negative $F_{4-38}$ seed was determined.

$F_{1-38A}$ seed of Event LY038 was field grown and allowed to self pollinate to produce $F_{2B}$ seed for which free lysine was determined.

$F_{4-38}$ seed of Event LY038 was field grown to produce $F_{4-38}$ plants and either A) self pollinated to produce $F_{5-38}$ seed, or B) crossed to an inbred line to produce hybrid $F_{1-38B}$ seed used for agronomic evaluation. $F_{5-38}$ seed of Event LY038 was field grown and either A) self pollinated to produce $F_{6-38}$ seed, or B) crossed to an inbred line maize variety to produce additional hybrid $F_{2C}$ seed used for additional agronomic evaluation.

Deposits of the Monsanto Company maize seed of Event LY038 disclosed above was generated through the self-pollinating of $F_{5-38}$ plants to produce $F_{6-38}$ seed and the self-pollinating of $F_{6-38}$ plants to produce $F_{7-38}$ seed. The American Type Culture Collection (Manassas, Va.) accession number for Event LY038 is PTA-5623.

Free lysine accumulation was monitored during the development of Event LY038 maize lines. The lysine accumulation values are summarized in Table 1 and represent the quantity of free lysine present in the mature grain on a dry weight basis, in parts-per-million.

Different methods are useful to evaluate the lysine content of mature kernels comprising Event LY038. Other methods known the art that are useful to detect and quantitate lysine are contemplated by the inventors of the present invention to provide similar findings of an increase in lysine content of seed of LY038.

Liquid chromatography-mass spectrophotometry/mass spectrophotometry (LC-MS/MS) was used to analyze free lysine in the maize kernels of Event LY038. Individual mature maize kernel samples of Event LY038 were first weighed, ground to a fine, homogeneous powder and extracted with an extraction solvent comprising methanol, water, and formic acid. In situations where kernels were bulked, approximately 30 mg of ground powder was used. Both liquid chromatography and multiple-reaction-monitoring (MRM) mass spectrometric techniques were used to separate lysine in the sample extract. After the separation, lysine was quantified using its mass spectrometry peak area against its corresponding standard calibration curve which was prepared using a deuterated $d_4$-lysine internal standard (IS).

In another method, lysine content of maize kernels was based upon evaluation of the free amino acids by high performance liquid chromatography (HPLC). Individual maize kernels or pools of kernels of Event LY038 were ground to a fine, homogenous powder as described, and in this instance, approximately 30 mg of powder was used for analysis. Amino acids were extracted with 5% trichloroacetic acid and amino acid detection was achieved through a pre-column primary amine derivatization with o-phthalaldehyde (OPA). The resulting amino acid adduct, an isoindole, is hydrophobic and possesses excellent fluorescence characteristics, which can then be detected on a fluorescence detector. Using reverse-phase chromatography, separation is achieved through the hydrophobicity of the R-groups located on each amino acid. To help stabilize the fluorophor, a thiol is added such as 2-mercaptoethanol ($SHCH_2CH_2OH$) or 3-mercaptopropionic acid ($SHCH_2CH_2COOH$).

Based on the experiments described here, free lysine in maize kernels that contain the LY038 construct increased between about 200% (e.g., $F_{1B}$, among others) and nearly 300% (e.g., $F_{1A}$). Intermediate increases in free lysine were also observed (e.g., $F_{1-38A}$).

Example 3

Determination of Flanking Sequence

Genomic DNA was isolated from maize plants designated as LY038 and used in experiments to determine the maize genomic sequence flanking the transgenic DNA insert. Three different methods for determining flanking sequences and the sequence of the junction between the genomic flanking sequence and transgenic insert were used: tail PCR and the Genome Walker™ kit from ClonTech (catalog number K1807-1, ClonTech Laboratories, Palo Alto, Calif.), and inverse PCR.

Tail PCR is a method for isolating genomic DNA sequence flanking a known inserted sequence which employs degenerative primers and a biotin capture step. A primer complementary to the exogenous DNA is used in primary PCR reactions together with a variety of degenerative primers. Typically, primers specific for the exogenous DNA and the degenerate primers were used in pairs and not in pools. The degenerate primers hybridize to some degree to the maize genomic sequence flanking the inserted DNA to allow for the

TABLE 1

Breeding scheme and lysine analysis used to identify high lysine maize Event LY038.

| Plant Generation | Molecular & Field analyses | Pollination | Seed Produced | LY038 Lysine efficacy* | Negative Control Lysine efficacy* |
| --- | --- | --- | --- | --- | --- |
| $R_0$ plant (Inbred A) | PCR; TaqMan copy number determination | Crossed with inbred line | $F_{1A}$ seed | ND | ND |
| $F_{1A}$ plant | NPTII field assay | Crossed with Cre recombinase line | $F_{1B}$ seed | +++ | − |
| $F_{1B}$ plant | PCR for DHDPS, Cre recombinase & NPTII; Southern Blot analysis | Self pollinate; positives and negatives selected and maintained | $F_{2A}$ seed | + | − |
| $F_{2A}$ plants (pos & neg) | PCR; Southern Blot analysis | Self pollinate | $F_3$ seed | + | − |
| $F_3$ plants (pos & neg) | PCR | Self pollinate; cross to inbred lines; select line LY038 | $F_{4-38}$ and $F_{1-38A}$ hybrid seed | +[i] | − |
| $F_{1-38A}$ plants (F3 plants × inbred) | | Self pollinate | $F_{2B}$ seed | ++ | − |
| $F_{4-38}$ plants (pos & neg) | Event-specific PCR | Self pollinate and cross to inbred lines | $F_{5-38}$ and $F_{1-38B}$ hybrid seed | +[i] | − |
| $F_{1-38B}$ plants (F$_{4-38}$ plants × inbred) | | Self pollinate | $F_{2C}$ seed | ++ | − |

*represents ppm free lysine in mature kernels comprising Event LY038
ND = not determined
− indicates less than about 400 ppm free lysine
+ indicates about 1000 to about 1200 ppm free lysine
++ indicates about 1200 to about 1400 ppm free lysine
+++ indicates greater than about 1400 ppm free lysine
[i] = inbred kernel data generation of PCR amplicons. The primary PCR amplicons are mixed with a biotin labeled primer complementary to the transgene portion of the amplicon and allowed to anneal. The amplicons annealed to the biotin primers were captured using streptavidin and unbound amplicons were washed away. The annealed amplicons were subjected to secondary PCR reactions utilizing a nested primer which was complementary to the exogenous DNA portion of the amplicon and a variety of degenerate primers. The PCR amplicons of the secondary PCR reaction were subjected to agarose gel electrophoresis and bands were cut from the gel and isolated. The isolated PCR amplicons were sequenced. The sequence of the 3' flanking genomic DNA of Event LY038 was identified using tail PCR and sequencing.

The Genome Walker method for isolation of flanking DNA was carried out according to manufacturer's suggested conditions. Both tail PCR and the Genome Walker Kit were used to identify the sequence of the 5' flanking DNA of Event LY038. For Genome Walker, products of the restriction enzyme ScaI were amplified to produce amplicons useful for identifying the 5' flanking genomic DNA sequence of Event LY038.

Use of the tail PCR and Genome Walker methods generated several hundred base pairs or more of DNA sequence flanking the insertion site of the DNA construct in Event LY038. Inverse PCR and bioinformatic analysis and comparison to maize genomic DNA sequence databases were used to obtain additional genomic DNA flanking these events. Using the combined methods, the flanking sequences are identified in the sequence of SEQ ID NOs: 1, 2, 9, and 10. A maize plant is an aspect of the present invention when that maize plant contains within its genome a DNA molecule that can be used as a template in a DNA amplification reaction to provide an amplicon comprising a junction DNA molecule described in the present invention, wherein the junction DNA molecule is diagnostic for corn Event LY038 DNA in a DNA sample extracted from a maize tissue sample.

Example 4

Event Specific Primer and Probe Assay Information

For each event, PCR primers and probes useful in a Taqman® assay were designed, namely SEQ ID NOs: 3 and 4. Using the PCR primers having the sequence of SEQ ID NOs: 3 and 4, in a Taqman® assay resulted in an amplicon diagnostic for Event LY038; the amplicon has the sequence of SEQ ID NO: 6, and the probe useful for the detection of this amplicon has the sequence of SEQ ID NO: 5. When the primers and probes were subjected to the PCR conditions outlined in Table 2, a fluorescent signal indicated that amplicons were produced that were detected by the probe. By inclusion of the appropriate control samples, for example, various negative and positive DNA controls, it was shown that the PCR primers and probes were specific for the intended event.

In addition to the primer and probe set, any primer and probe sets derived from SEQ ID NO: 1 or 2, specific for Event LY038 DNA that when used in a PCR amplification reaction produce a DNA amplicon diagnostic for Event LY038 DNA are an aspect of the present invention and are readily prepared by those of skill in the art. PCR conditions to produce a Taqman® assay diagnostic for Event LY038 DNA are included in Table 2.

One skilled in the art would include the appropriate control samples when performing the PCR or Taqman® assays described in the present invention. The inclusion of positive control DNA samples, negative control DNA samples, and other controls are appropriate and aid in the interpretation of results. In addition, the person of ordinary skill in the art would know how to prepare internal control primers and probes for the Taqman® PCR reaction using published, standard methods (as published by, for example, Applied Biosystems, Foster City, Calif.). One skilled would also realize that the particular primer sequences, probes, and reaction conditions specified herein may be modified and produce an assay which is diagnostic for Event LY038 DNA. Additionally, one skilled in the art would know that the products of the PCR reaction may be analyzed by gel electrophoresis for analysis.

TABLE 2

PCR reaction mixture and conditions diagnostic for LY038 event DNA

| Step | Reagent | Volume | Comments |
|---|---|---|---|
| 1 | 18 megohm water | Adjust for final volume of 10 µl | e.g. Sigma Catalog #W-4502 |
| 2 | 2X Universal Master Mix | 5 µl | Applied Biosystems, Palo Alto, CA; Part # 4304437; 1X final concentration of buffer |
| 3 | Mixture of event-specific primers (SEQ ID NOs: 3 and 4)* | 0.5 µl | 1 µM final concentration |
| 4 | Event-specific probe FAM label (SEQ ID NO: 5)** | 0.2 µl | 200 µM final concentration |
| 5 | Mixture of internal control primers*,^ | 0.5 µl | 1 µM final concentration |
| 6 | Internal control probe VIC label | 0.2 µl | 200 µM final concentration |
| 7 | DNA template*** | 3.0 µl | Preferably 5-10 ng per reaction |
| 8 | Amplification Cycle | | |

| No. | Settings |
|---|---|
| 1 | 50° C. 2 minutes |
| 1 | 95° C. 10 minutes |
| 10 | 95° C. 15 seconds 64° C. 1 minute −1° C./cycle |
| 30 | 95° C. 15 seconds 54° C. 1 minute |
| 1 | 10° C. forever |

| Step | Reagent | | Comments |
|---|---|---|---|
| 9 | Analysis of PCR reaction | | Applied Biosystems Gene|Amp PCR System 9700 or fluorescent plate reader |

*Resuspend mixed primers in 18 megohm water to a concentration of 20 µM each primer. Example: 100 µl first primer at a concentration of 100 µM, 100 µl second primer at a concentration of 100 µM, 300 µl 18 megohm water.
**Resuspend probe in 18 megohm water to a concentration of 10 µM.
***May include but not be limited to: negative DNA control (e.g., non-transgenic DNA) negative water control (no template DNA) positive control (Event LY038) sample DNA (from leaf, seed, other plant part samples)
^Internal control primer and probe combinations may be made to a wide variety of genes or genomic regions, the design of which is known to those of skill in the art.

Deposits of the Monsanto Company maize seed representative of Event LY038 disclosed above have been made under the Budapest Treaty with the American Type Culture Collection (ATCC), 10801 University Boulevard, Manassas, Va. 20110, on Oct. 29, 2003. The ATCC accession number for Event LY038 is PTA-5623. The deposit will be maintained in the depository for a period of 30 years, or 5 years after the last request, or for the effective life of the patent, whichever is longer, and will be replaced as necessary during that period. All restrictions on the accessibility of the deposited biological material will be irrevocably removed upon the grant of a patent on the current invention.

Having illustrated and described the principles of the present invention, it should be apparent to persons skilled in the art that the present invention can be modified in arrangement and detail without departing from such principles. We claim all modifications that are within the spirit and scope of the appended claims.

The invention claimed is:

1. A pair of DNA primer molecules comprising: a first DNA molecule and a second DNA molecule, wherein said first DNA molecule comprises at least 18 contiguous nucleotides from nucleotide 1 to 200 of SEQ ID NO:2 or its full complement, and said second DNA molecule comprises at least 18 contiguous nucleotides from nucleotide 201 to 867 of SEQ ID NO:2 or its full complement and wherein said pair of DNA primer molecules when used together in a DNA amplification reaction produce a diagnostic amplicon comprising SEQ ID NO:11 or full complements thereof.

2. A method of determining the presence of DNA corresponding to the genomic/transgene DNA of maize LY038 Event in a maize tissue sample comprising the steps of:
(a) obtaining DNA from the maize tissue sample;
(b) contacting said DNA with a primer pair according to claim 1;
(c) amplifying said DNA with said primer pair, thereby producing a DNA amplicon comprising at least base pairs 200 to 201 of SEQ ID NO:2 or its complement; and
(d) detecting said DNA amplicon.

3. A stably transformed maize plant, that when analyzed by the method of claim 2, produces a DNA amplicon comprising SEQ ID NO:11.

4. The method according to claim 2, wherein said maize tissue sample is derived from a maize seed of Event LY038 or a plant grown from said seed of Event LY038, wherein a representative sample of said Event LY038 has been deposited with the American Type Culture Collection as ATCC seed deposit PTA-5623.

5. A DNA detection kit for maize Event LY038 comprising: at least one of the following: (a) an isolated probe comprising SEQ ID NO:11, or (b) said primer pair of claim 1, wherein a representative sample of said Event LY038 has been deposited with the American Type Culture Collection as ATCC seed deposit PTA-5623.

6. A DNA molecule comprising SEQ ID NO:2 or fragments therefrom comprising SEQ ID NO:11.

7. A maize plant, seed or part thereof, comprising maize Event LY038, wherein a representative sample of said Event LY038 has been deposited with the American Type Culture Collection as ATCC seed deposit PTA-5623.

8. A maize plant, seed, cell, endosperm, or meal comprising the DNA molecule of claim 6.

9. A DNA molecule comprising SEQ ID NO:2 or SEQ ID NO:11.

10. A method of determining the presence of DNA corresponding to the genomic/transgene DNA of maize LY038 Event in a maize tissue sample comprising the steps of:

(a) obtaining a DNA sample from said maize tissue;
(b) contacting said DNA sample with a probe comprising at least 18 nucleotides of SEQ ID NO:11 or its complement; and
(c) detecting hybridization of said probe to said DNA, wherein hybridization of said probe is diagnostic of maize Event LY038, wherein a representative sample of said Event LY038 has been deposited with the American Type Culture Collection as ATCC seed deposit PTA-5623.

11. The method of claim 10, wherein said probe is selected from the group consisting of SEQ ID NO:2 or fragments therefrom comprising SEQ ID NO:11.

* * * * *

SEQUENCE LISTING

<160> NUMBER OF SEQ ID NOS: 11

<210> SEQ ID NO 1
<211> LENGTH: 1961
<212> TYPE: DNA
<213> ORGANISM: Artificial sequence
<220> FEATURE:
<223> OTHER INFORMATION: Zea mays flank and portion of transgene

<400> SEQUENCE: 1

```
ataaaccagc tcccttcgag gggcttcaag ctcatgaaca aggcagacgg gaagcacagg      60
aacttcggta tatctcgaat ctctggcgag gcagttgcta ctcgacggaa ctagtcagct     120
gaaggtcttt ttgctattgg aattcaatag gaggcgggag ctaactgaca ccatgccgcc     180
ctagttttgt tgaactgata gtggtgctag ccttgtgcat agtagggggcc aggggagtaa    240
taatatttcc cttgtctaag gaagtgatta aggatgtagg agcacagcgc aaatgattag     300
caaaacgatc acgttcgcag tgcggcaggc attgcgcagc tggttcgttt gttcaatcag     360
tgctctcgct cacagtgacc tgacagcgtg atcactaaac ctagtagctg ggcgcgcctt     420
tctagatcag aacggaacat tggcactgga ttagattcca gtgcggcatg cttcgaaagc     480
gaggacacgg gtgctcccta agtacatgtt ttgaatggat gtggagtggc ccgtccattc     540
cgcattccaa tgggcctgtt tggttcagct ttttctgac cagcttttct gagaatctgg      600
ctgtggggag aatctggctg tgtagagaat ctgagtatca ttaggattac gtgcggagga    660
agataaaggt gtccatagga ctcaggatgt agaaagtgac ggattcctac tattgcaacg     720
actcaaccga ttatgtgttt atgttgattt tgaatggttt tacccaaac gaattttata      780
gaagttgact gaaaagctga cgtttggca gtccgcaaca gcttttggtg ccagaagct       840
ccaaaaagct gaaacaaaca ggggcaatag ttgacgcttt ggacgtctca agcctggccg     900
tcaggcgctg taccccagct ggctgttcag agctacaaca ctactcggga gtttttttt      960
gtctcaccta taaaaagaa cataaaataa agaactactg ctacgactca caggccagaa    1020
gtcagaacga cgacacagtg gcaactctcg tccatcgtca ttttctgcgt ggcggtacgc    1080
atgcataggg tcgccgttga ttcctactcg tatactttac ctgaacaccg ctgcatgcac    1140
gcctggacaa agataacgag gaaacgtcca gtcgctagct ctgacagtgt tggacgtttt    1200
accgctgcaa tcactattac gggatgcatt tgatatctgg agagtacgtt gcgcgaagac    1260
gcagtttgcg aagcctggtc gtgctcgtgc acctgcattg cagttcattt cagtcgctcg    1320
agcactcctc atccccacc atcgtcacca cttttcgggt ttggtttggt attttcccgc     1380
acgcacgggg gccccgaggt gtgtgacact gtgactggac acccaaagcc tagccaagca   1440
agcggaagaa cgcaacgcaa agcaggtcag ctcctccgtc cgaattcagc ctgttactcg    1500
ttcgctcact ttcctctccc tttctctccc cgccatcttc cttaaatctt ttcttccagt    1560
aaccttttcgc cgcaaaatcc gtgcttccga gtcgagtatt ggactcgctg cctggtttcg   1620
ttttttttat gatgagagaa agagagagag gaaaggtaat ccgtcctgtt ttgatgatgt    1680
gcctgctgag atttaaggct gcattgtggg ttcagtctgc gaatgtttgg gggtgggggc    1740
caatccctgc gcagaatctc aggatccgag cggagtttat gggtcgacgg tatcgataag    1800
cttgatatcg aattcctgca gcccgggccg agtgccatcc ttggacactc gataaagtat    1860
atttttatttt ttttattttg ccaaccaaac ttttgtggt atgttcctac actatgtaga    1920
tctacatgta ccatttggc acaattacat atttacaaaa a                         1961
```

-continued

```
<210> SEQ ID NO 2
<211> LENGTH: 867
<212> TYPE: DNA
<213> ORGANISM: Artificial sequence
<220> FEATURE:
<223> OTHER INFORMATION: Zea mays flank and portion of transgene

<400> SEQUENCE: 2
cgttcgttct cagcatcgca actcaatttg ttatggcgga gaagcccttg tatcccaggt      60
agtaatgcac agatatgcat tattattatt cataaaagaa ttcgaggggg atccataact     120
tcgtatagca tacattatac gaagttattc tagagcggcc gccaccgcgg tggagctcgg     180
atccactagt aacggccgcc ataattattg cccagtcttt cagggtatta cagtgtacaa     240
tgtttcagta ttttagactg cactactata atatcacaag aactcaaaat ggagcattca     300
atactactag tacaatgagt gtgcattgcg acggcacaca aattattcaa taaaatatta     360
gtggacaata attacatgaa aacgaaccaa ttaagatgtc cgcttgaagt gccttttggg     420
tcaattacat agctcccctg caaatggagc attcaatact ttcctgtccg cttgaaatgc     480
cttttgggtc aattacatag ctcccctgca aattaagatg tcaaatatac tatcacataa     540
ccatcccaaa ggataaacca ggatcaccaa acacacaata ccaattgatc tcagacaggc     600
acatccaaca ttgcttgaat ctcaagtaaa acaattccag atctatcttg tataagtaaa     660
agagctttct gatccaagac atgcttttct gaatctcaag taaaacaata ccagacaggc     720
acattacttg ctttctgatc caagacatgc tttgactcag aatccactca agtataacac     780
catatattta tatatctttt agttgagtaa acatgcaat catcaatgaa gataaacccc     840
ctgcttataa tgaatcaggc ttataac                                          867

<210> SEQ ID NO 3
<211> LENGTH: 20
<212> TYPE: DNA
<213> ORGANISM: Artificial sequence
<220> FEATURE:
<223> OTHER INFORMATION: PCR primer

<400> SEQUENCE: 3
aatccctgcg cagaatctca                                                   20

<210> SEQ ID NO 4
<211> LENGTH: 25
<212> TYPE: DNA
<213> ORGANISM: Artificial sequence
<220> FEATURE:
<223> OTHER INFORMATION: PCR primer

<400> SEQUENCE: 4
tgcaggaatt cgatatcaag cttat                                             25

<210> SEQ ID NO 5
<211> LENGTH: 16
<212> TYPE: DNA
<213> ORGANISM: Artificial sequence
<220> FEATURE:
<223> OTHER INFORMATION: Probe

<400> SEQUENCE: 5
cggagtttat gggtcg                                                       16

<210> SEQ ID NO 6
<211> LENGTH: 79
<212> TYPE: DNA
```

```
<213> ORGANISM: Artificial sequence
<220> FEATURE:
<223> OTHER INFORMATION: PCR product amplicon

<400> SEQUENCE: 6
aatccctgcg cagaatctca ggatccgagc ggagtttatg ggtcgacggt atcgataagc    60
ttgatatcga attcctgca                                                 79

<210> SEQ ID NO 7
<211> LENGTH: 4176
<212> TYPE: DNA
<213> ORGANISM: Artificial sequence
<220> FEATURE:
<223> OTHER INFORMATION: Exogenous DNA

<400> SEQUENCE: 7
ggtcgacggt atcgataagc ttgatatcga attcctgcag cccgggccga gtgccatcct    60
tggacactcg ataaagtata tttttatttt tttattttgc caaccaaact ttttgtggta   120
tgttcctaca ctatgtagat ctacatgtac cattttggca caattacata tttacaaaaa   180
tgttttctat aaatattaga tttagttcgt ttatttgaat tcttcggaa aattcacatt    240 taaactgcaa gtcactcgaa acatggaaaa ccgtgcatgc aaaataaatg atatgcatgt   300
tatctagcac aagttacgac cgatttcaga agcagaccag aattttcaag caccatgctc   360
actaaacatg accgtgaact tgttatctag ttgtttaaaa attgtataaa acacaaataa   420
agtcagaaat taatgaaact tgtccacatg tcatgatatc atatatagag gttgtgataa   480
aaatttgata atgtttcggt aaagttgtga cgtactatgt gtagaaacct aagtgaccta   540
cacataaaat catagagttt caatgtagtt cactcgacaa agactttgtc aagtgtccga   600
taaaaagtac tcgacaaaga agccgttgtc gatgtactgt tcgtcgagat ctctttgtcg   660
agtgtcacac taggcaaagt ctttacggag tgtttttcag gctttgacac tcggcaaagc   720
gctcgattcc agtagtgaca gtaatttgca tcaaaaatag ctgagagatt taggccccgt   780
ttcaatctca cgggataaag tttagcttcc tgctaaactt tagctatatg aattgaagtg   840
ctaaagttta gtttcaatta ccaccattag ctctcctgtt tagattacaa atggctaaaa   900
gtagctaaaa aatagctgct aaagtttatc tcgcgagatt gaaacagggc cttaaaatga   960
gtcaactaat agaccaacta attattagct attagtcgtt agcttcttta atctaagcta  1020
aaaccaacta atagcttatt tgttgaatta caattagctc aacggaattc tctgtttttt  1080
taaaaaaaaa ctgcccctct cttacagcaa attgtccgct gcccgtcgtc cagatacaat  1140
gaacgtacct agtaggaact cttttacacg ctcggtcgct cgccgcggat cggagtcccc  1200
ggaacacgac accactgtgg aacacgacaa agtctgctca gaggcggcca cccctggcg   1260 tgcaccgagc cggagcccgg ataagcacgg taaggagagt acggcgggac gtggcgaccc  1320
gtgtgtctgc tgccacgcag ccttcctcca cgtagccgcg cggccgcgcc acgtaccagg  1380
gcccggcgct ggtataaatg cgcgccacct ccgctttagt tctgcataca gccaacccaa  1440
ggatcccctc gaaattcggt aaccaccccg cccctctcct ctttctttct ccgtttttt   1500 tttccgtctc ggtctcgatc tttggccttg gtagtttggg tgggcgagag gcggcttcgt  1560
gcgcgcccag atcggtgcgc gggaggggcg ggatctcgcg gctggggctc tcgccggcgt  1620
ggatccggcc cggatctcgc ggggaatggg gctctcggat gtagatctgc gatccgccgt  1680
tgttggggga gatgatgggg ggtttaaaat ttccgccatg ctaaacaaga tcaggaagag  1740
gggaaaaggg cactatggtt tatatttta tatatttctg ctgcttcgtc aggcttagat  1800
```

```
gtgctagatc tttctttctt cttttttgtgg gtagaatttg aatccctcag ctttgttcat    1860
cggtagtttt tcttttcatg atttgtgaca aatgcagcct cgtgcggagc tttttttgtag   1920
gtagccacca tggtttcgcc gacgaatctc ctcccggcgc ggaagatcac ccctgtctca    1980
aatggcggcg cagcgacggc gagcccctct tctccctcgg tggccgcacg gccacggcga    2040
ctcccttcag gcctccaatc tgtgactggt agagggaagg tttccttggc agccatcact    2100
agtacaggtt taacagctaa gaccggagta gagcacttcg gcaccgttgg agtagcaatg    2160
gttactccat tcacggaatc cggagacatc gatatcgctg ctggccgcga agtcgcggct    2220
tatttggttg ataagggctt ggattctttg gttctcgcgg gcaccactgg tgaatcccca    2280
acgacaaccg ccgctgaaaa actagaactg ctcaaggccg ttcgtgagga agttggggat    2340
cgggcgaagc tcatcgccgg tgtcggaacc aacaacacgc ggacatctgt ggaacttgcg    2400
gaagctgctg cttctgctgg cgcagacggc cttttagttg taactcctta ttactccaag    2460
ccgagccaag agggattgct ggcgcacttc ggtgcaattg ctgcagcaac agaggttcca    2520
atttgtctct atgacattcc tggtcggtca ggtattccaa ttgagtctga taccatgaga    2580
cgcctgagtg aattacctac gattttggcg gtcaaggacg ccaagggtga cctcgttgca    2640
gccacgtcat tgatcaaaga aacgggactt gcctggtatt caggcgatga cccactaaac    2700
cttgtttggc ttgctttggg cggatcaggt ttcattccg taattggaca tgcagccccc     2760
acagcattac gtgagttgta cacaagcttc gaggaaggcg acctcgtccg tgcgcgggaa    2820
atcaacgcca aactatcacc gctggtagct gcccaaggtc gcttgggtgg agtcagcttg    2880
gcaaaagctg ctctgcgtct gcagggcatc aacgtaggag atcctcgact tccaattatg    2940
gctccaaatg agcaggaact tgaggctctc cgagaagaca tgaaaaaagc tggagttcta    3000
taatgatcta gagcaagccg aattcctgca gcccggggga tccactagtt ctagagcggc    3060
cgccaccgcg gtggagctcg ccaaaacgag caggaagcaa cgagagggtg gcgcgcgacc    3120
gacgtgcgta cgtagcatga gcctgagtgg agacgttgga cgtgtatgta tatacctctc    3180
tgcgtgttaa ctatgtacgt aagcggcagg cagtgcaata agtgtggctc tgtagtatgt    3240
acgtgcgggt acgatgctgt aagctactga ggcaagtcca taaataaata atgacacgtg    3300
cgtgttctat aatctcttcg cttcttcatt tgtccccttg cggagtttgg catccattga    3360
tgccgttacg ctgagaacag acacagcaga cgaaccaaaa gtgagttctt gtatgaaact    3420
atgacccttc atcgctaggc tcaaacagca ccccgtacga acacagcaaa ttagtcatct    3480
aactattagc ccctacatgt ttcagacgat acataaatat agcccatcct tagcaattag    3540
ctattggccc tgcccatccc aagcaatgat ctcgaagtat ttttaatata tagtattttt    3600
aatatgtagc ttttaaaatt agaagataat tttgagacaa aaatctccaa gtattttttt    3660
gggtatttt tactgcctcc gttttctctt atttctcgtc acctagttta attttgtgct      3720
aatcggctat aaacgaaaca gagagaaaag ttactctaaa agcaactcca acagattaga    3780
tataaatctt atatcctgcc tagagctgtt aaaaagatag acaactttag tggattagtg    3840
tatgcaacaa actctccaaa tttaagtatc ccaactaccc aacgcatatc gttccctttt    3900
cattggcgca cgaactttca cctgctatag ccgacgtaca tgttcgtttt ttttgggcgg    3960
cgcttacttt cttccccgtt cgttctcagc atcgcaactc aatttgttat ggcggagaag    4020
cccttgtatc ccaggtagta atgcacagat atgcattatt attattcata aaagaattcg    4080
agggggatcc ataacttcgt atagcataca ttatacgaag ttattctaga gcggccgcca    4140
ccgcggtgga gctcggatcc actagtaacg gccgcc                              4176
```

<210> SEQ ID NO 8
<211> LENGTH: 903
<212> TYPE: DNA
<213> ORGANISM: Corynebacterium glutamicum

<400> SEQUENCE: 8

| | | | | | |
|---|---|---|---|---|---|
| agtacaggtt | taacagctaa | gaccggagta | gagcacttcg | gcaccgttgg | agtagcaatg | 60 |
| gttactccat | tcacggaatc | cggagacatc | gatatcgctg | ctggccgcga | agtcgcggct | 120 |
| tatttggttg | ataagggctt | ggattctttg | gttctcgcgg | gcaccactgg | tgaatcccca | 180 |
| acgacaaccg | ccgctgaaaa | actagaactg | ctcaaggccg | ttcgtgagga | agttggggat | 240 |
| cgggcgaagc | tcatcgccgg | tgtcggaacc | aacaacacgc | ggacatctgt | ggaacttgcg | 300 |
| gaagctgctg | cttctgctgg | cgcagacggc | cttttagttg | taactcctta | ttactccaag | 360 |
| ccgagccaag | agggattgct | ggcgcacttc | ggtgcaattg | ctgcagcaac | agaggttcca | 420 |
| atttgtctct | atgacattcc | tggtcggtca | ggtattccaa | ttgagtctga | taccatgaga | 480 |
| cgcctgagtg | aattacctac | gattttggcg | gtcaaggacg | ccaagggtga | cctcgttgca | 540 |
| gccacgtcat | tgatcaaaga | aacgggactt | gcctggtatt | caggcgatga | cccactaaac | 600 |
| cttgtttggc | ttgctttggg | cggatcaggt | ttcatttccg | taattggaca | tgcagccccc | 660 |
| acagcattac | gtgagttgta | cacaagcttc | gaggaaggcg | acctcgtccg | tgcgcgggaa | 720 |
| atcaacgcca | aactatcacc | gctggtagct | gcccaaggtc | gcttgggtgg | agtcagcttg | 780 |
| gcaaaagctg | ctctgcgtct | gcagggcatc | aacgtaggag | atcctcgact | tccaattatg | 840 |
| gctccaaatg | agcaggaact | tgaggctctc | cgagaagaca | tgaaaaaagc | tggagttcta | 900 |
| taa | | | | | | 903 |

<210> SEQ ID NO 9
<211> LENGTH: 1736
<212> TYPE: DNA
<213> ORGANISM: Zea mays

<400> SEQUENCE: 9

| | | | | | |
|---|---|---|---|---|---|
| gaatccctca | gctttgttca | tcggtagttt | ttctttcat | gatttgtgac | aaatgcagcc | 60 |
| tcgtgcggag | cttttttgta | ggtagccacc | atggagtgca | caccggtctc | tactctagtc | 120 |
| gcaacatttg | caccctcacg | acgctgcgac | tgcgggggga | tttcaacccg | tcggctccta | 180 |
| tcttcggctt | ctactctagt | ctcatcgtgt | gtggtgcccc | gttgcaactg | cgggggggatg | 240 |
| ttagactgtg | tgtgggctgg | caccactgtt | ggctgccga | cccattaggg | ttagggttaa | 300 |
| gtctctctat | gtatgtaccc | cttctctatg | caatagatta | agcattaggg | tttcctacac | 360 |
| acaccaggat | tttaagtgaa | caaatgtgcc | cctttacaaa | ctaacaatga | ccatgaaatg | 420 |
| cctaagatta | ccaatgatcc | aagaccagga | attttttatta | ttttgtggtg | ttgcttttgt | 480 |
| aagctaatta | ggttgtttat | ttttggtgct | ttatagttgt | ccaaccttat | tgccttttcc | 540 |
| accaattggg | tacactcatt | cttcaacaca | ttcattaact | atttcatgtt | ttttaacttt | 600 |
| gaactgcgct | tatctctgtt | cttttatttt | atgacttgga | tgaaataagt | cagttagtcg | 660 |
| tattaaccat | ttggctgcca | ttttacatgt | gatagattat | ttatttcttg | attcctgata | 720 |
| gttttttta | ttcgtggctt | ctactgttct | aaatatgaact | atggactaaa | tattttattt | 780 |
| tgatttcctg | ctacttgcag | attgaaatgt | cggagatacg | tgctttagtc | agccgagcta | 840 |
| ctgctaggag | tcttgttctg | attgatgaaa | tatgtgagg | cacagaaact | gcaaaaggaa | 900 |
| catgtatagc | tggtagcatc | attgaaagac | ttgataatgt | tggctgccta | ggcatcatat | 960 |

-continued

```
caactcacct gcatgggatt ttcgacctgc ctctctcact tagcaacact gatttcaaag    1020
ctatgggaac tgaagtggtc gatggatgca ttcatccaac atggaaactg attgatggca    1080
tatgtagaga aagccttgct tttcaaacag caaggaggga aggcatgcct gacttgataa    1140
tcaccagggc tgaggagcta tatttgagta tgagtacaaa taacaagcag ggagcatcag    1200
tggcgcacaa tgagcctcct aatggcagcc ccagtgtaaa tggcttggtt gaggagcctg    1260
aatctctgaa gaacagactg gaaatgctgc ctggtacctt tgagccgctg cggaaggaag    1320
ttgagagtgc tgttactacg atgtgtaaga aaatactgtc ggacctttac aacaaaagta    1380
gcatcccaga actggtcgag gtggtctgcg ttgctgtagg tgctagagag caaccaccgc    1440
cttccactgt tggcagatct agcatctacg tgattatcag aagcgacaac aggctctatg    1500
ttggacaggt aaattcatga tcgcatttttt ttttctgcgt tgttcattat ctcaggtgat    1560
acagccccat aaaatgccga cactgacgac agatctcctt tttttctgcc tgcagacgga    1620
cgatcttctg gggcgcttga acgccccaca gatcgaagga aggcatgcgg gacgctacgg    1680
tattatacgt cttggtccct ggcaagagcg ttgcctgcca gctggaaacc cttctc        1736
```

<210> SEQ ID NO 10
<211> LENGTH: 359
<212> TYPE: DNA
<213> ORGANISM: Zea mays

<400> SEQUENCE: 10

```
aatgaagata aacccoctgc ttataatgaa tcaggcttat aacaacaaat tataatatga      60
aggatttaat taactttagt tttcttcaaa cttgtagctg accatatatt tatatatctt     120
ttagttgagt aaaacatgca atcatttctt taggcttctc ctttctagta cttataattt     180
caccttctct ataatagtat tcagaagtaa atgtatcctt taaaatagta ctcagattta     240
tttttaattt ttttcatttt tgttagccag tttcttttct ttgtgttatt ctacgattca     300
ggttcaacat taattaaatc tgaaacgcac aaacacattt aaaggaaagt gggaagctt      359
```

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11

```
aacggccgcc ataattattg                                                  20
```